United States Patent [19]

Ogawa

[11] 4,293,762
[45] Oct. 6, 1981

[54] TEMPERATURE-CONTROLLED ELECTRIC HEATING DEVICE FOR HEATING INSTILLATION OR TRANSFUSION LIQUIDS

[76] Inventor: Genshirou Ogawa, 13-3, Inuyama Nishikoken, Inuyama, Aichi-ken, Japan

[21] Appl. No.: 964,861

[22] Filed: Nov. 30, 1978

[30] Foreign Application Priority Data

Feb. 16, 1978 [JP] Japan ................................. 53-16909

[51] Int. Cl.³ ..................... H05B 1/02; A61M 5/14; F24H 1/14
[52] U.S. Cl. ................................ 219/302; 128/214 A; 128/401; 165/46; 219/305; 219/308; 219/330; 219/501; 222/146 HE
[58] Field of Search ............... 219/301, 302, 303, 304, 219/305, 296, 299, 298, 280, 330, 501, 328; 128/214 A, 399, 401; 222/146 HE, 146 R, 146 H; 16/150; 165/46

[56] References Cited

U.S. PATENT DOCUMENTS

| | | | |
|---|---|---|---|
| 2,102,523 | 12/1937 | Ferrara et al. | 128/214 A |
| 2,470,481 | 5/1949 | Freeman | 219/280 X |
| 2,687,157 | 8/1954 | Cowan | 16/150 X |
| 3,293,868 | 12/1966 | Gonzalez | 219/303 X |
| 3,485,245 | 12/1969 | Lahr et al. | 219/302 X |
| 3,551,940 | 1/1971 | Edison | 16/150 |
| 3,590,215 | 6/1971 | Anderson et al. | 219/299 X |

FOREIGN PATENT DOCUMENTS

| | | | |
|---|---|---|---|
| 2619438 | 11/1977 | Fed. Rep. of Germany | 128/214 A |
| 2331230 | 6/1977 | France | 219/301 |
| 1446412 | 8/1976 | United Kingdom | 219/302 |

OTHER PUBLICATIONS

"Low Profile, Explosion-Proof Hot Plate"; Delgado et al.; IBM Technical Disclosure Bulletin; vol. 8, No. 12, May 1966, p. 1859.

*Primary Examiner*—A. Bartis
*Attorney, Agent, or Firm*—Jordan and Hamburg

[57] ABSTRACT

A heating device comprises a casing to be disposed vertically, the casing including a circuit element receiving chamber and a heater receiving chamber having a front opening, a lid for at least covering the front opening of the heater receiving chamber, a heater situated in the heater receiving chamber, and electric circuit means situated in the circuit element receiving chamber. The heater includes a heater segment coextensive with and disposed in the front opening and an electric heating element attached to a back side of the heater segment. The heater segment has a tortuous groove on a front side thereof to receive therein a liquid feed pipe through which an instillation liquid to be heated flows. The groove includes at least upper and lower curves and extends from an upper portion of the heater segment to a lower portion thereof through the curves to keep the instillation liquid in the liquid feed pipe between the upper and lower curves for a period sufficient to heat the liquid. The electric circuit means includes first and second temperature control thermistors, the first thermistor sensing temperature of the instillation liquid after passing through the heater segment for intermittently energizing the heater to heat the instillation liquid to a predetermined temperature. The second thermistor is provided at the electric heating element to turn off the electric circuit means when the electric heating element is heated beyond a predetermined temperature due to excessive flow of the instillation liquid to thereby override the control of the heater by the first thermistor.

3 Claims, 12 Drawing Figures

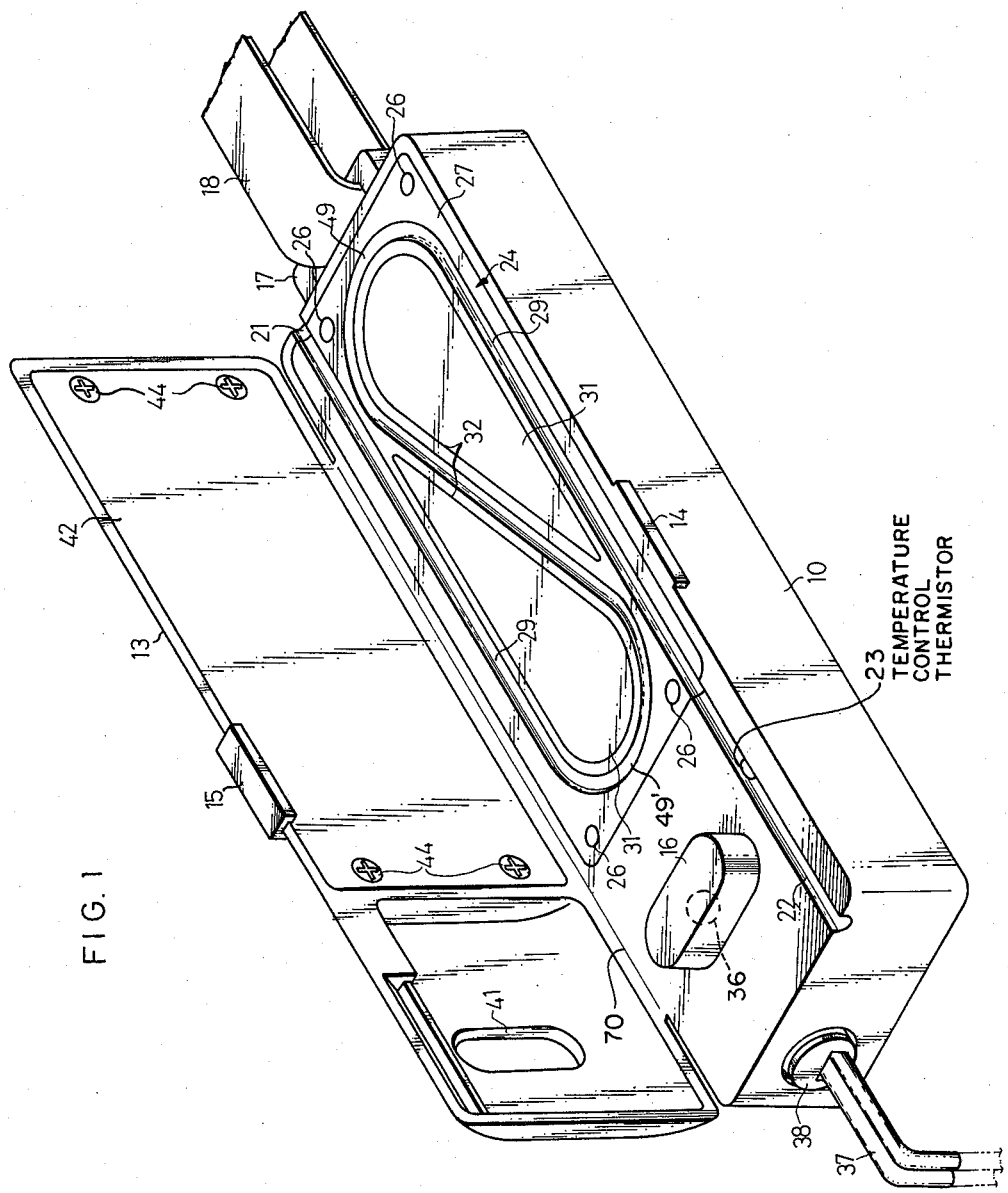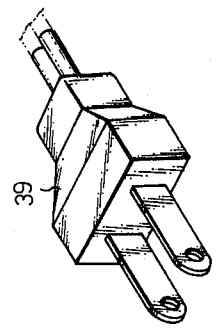

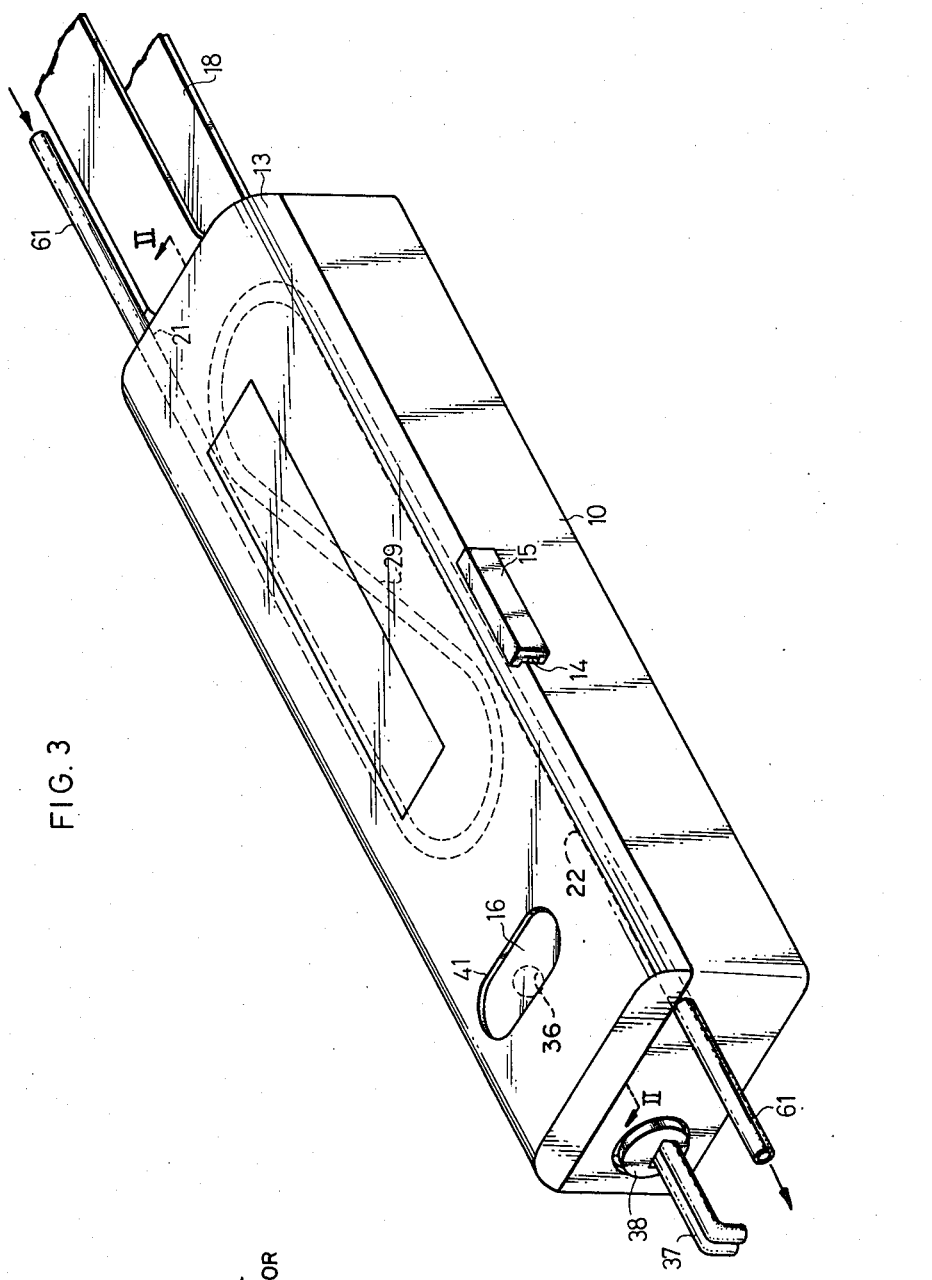

TEMPERATURE-CONTROLLED ELECTRIC HEATING DEVICE FOR HEATING INSTILLATION OR TRANSFUSION LIQUIDS

BACKGROUND OF THE INVENTION (1) Field of the Invention

The present invention relates to a heating device for instillation. More particularly, the invention relates to a heating device for injecting an instillation liquid, a blood transfusion liquid and or the like into a blood vessel of a patient at an optimum temperature.

(2) Description of the Prior Art

According to a conventional technique for heating an instillation liquid or blood transfusion liquid and injecting the heated liquid into a blood vessel of a patient, a liquid feed pipe is passed through a warm water tank to heat the liquid passing therethrough up to an appropriate temperature. According to this conventional technique, a large-size heating device must be used for heating water in the warming tank, and therefore, it takes time to get ready for instillation. Further, handling or transferring of the heating device is very troublesome.

OBJECTS AND SUMMARY OF THE INVENTION

It is a primary object of the present invention to provide a heating device for instillation, which has a small size, so as not to occupy a large space and to be transferred and handled very easily, and which can improve efficiency of the instillation operation, for example, dripping or blood transfusion.

Another object of the present invention is to provide a heating device for instillation, in which a heater can be effectively utilized for heating an instillation liquid or blood transfusion liquid. Heat of the heater is transferred to the liquid through a pipe at a high efficiency without loss of heat so that uneven heating for the instillation liquid or blood transfusion liquid can be completely prevented.

Still another object of the present invention is to provide a heating device for instillation, in which a liquid feed pipe through which the liquid to be heated blows is bent in an S-figured shape on a heater to increase contact area between the pipe and the heater, so that uneven heating can be completely prevented when the instillation liquid or blood transfusion liquid is heated.

A further object of the present invention is to provide a heating device for instillation, in which temperature overshooting of an instillation liquid is prevented during heating of the instillation liquid by diminishing the thermal capacity of a heater and the instillation liquid can be stably heated at a predetermined temperature in a short time.

A still further object of the present invention is to provide a heating device for instillation, which can be hung at a predetermined position to be freely adjusted in the vertical direction.

Other objects of the present invention will be apparent from embodiments described hereinafter and be clarified in appended claims. Various advantages of the present invention will be apparent to those skilled in the art when the present invention is practically carried out.

In accordance with the invention, there is provided a heating device for instillation. The heating device comprises a casing to be disposed vertically, the casing including a circuit element receiving chamber and a heater receiving chamber having a front opening, a lid for at least covering the front opening of the heater receiving chamber, a heater situated in the heater receiving chamber, and electric circuit means situated in the circuit element receiving chamber. The heater includes a heater segment disposed in the front opening and an electric heating element attached to a back side of the heater segment. The heater segment has a tortuous groove on a front side thereof to receive therein a liquid feed pipe through which an instillation liquid to be heated flows. The groove includes at least upper and lower curves and extends from an upper portion of the heater segment to a lower portion thereof through the curves to keep the instillation liquid in the liquid feed pipe between the upper and lower curves for a time sufficient to heat the liquid. The electric circuit means includes first and second temperature control thermistors, the first thermistor sensing temperature of the instillation liquid after passing through the heater segment for intermittently energizing the heater to heat the instillation liquid to a predetermined temperature. The second thermistor is provided at the electric heating element to turn off the electric circuit means when the electric heating element is heated beyond a predetermined temperature due to excessive flowing of the instillation liquid to thereby override the control of the heater by the first thermistor.

The lid includes a pressing member to intimately hold the liquid feed pipe in the groove when the lid is closed. Insulating materials are provided between the lid and the pressing member and between the casing and the electric heating element.

The casing and lid are integrally formed of a soft synthetic resin and are joined by an integral hinge so that the lid can be freely opened and closed. An anchoring projection and a hook are provided on the casing and the lid respectively to keep the lid closed.

BRIEF DESCRIPTION OF THE DRAWING

FIG. 1 is a perspective view illustrating one embodiment of the heating device for instillation according to the present invention in which a lid is opened.

FIG. 2 is a sectional view of the heating device taken along line II—II in FIG. 3.

FIG. 3 is a perspective view illustrating the manner in which a liquid feed pipe is situated in the heating device and the lid is closed.

DETAILED DESCRIPTION OF THE PREFERRED EMBODIMENTS

One embodiment of the heating device of the present invention will now be described with reference to the accompanying drawing.

Figure 4:
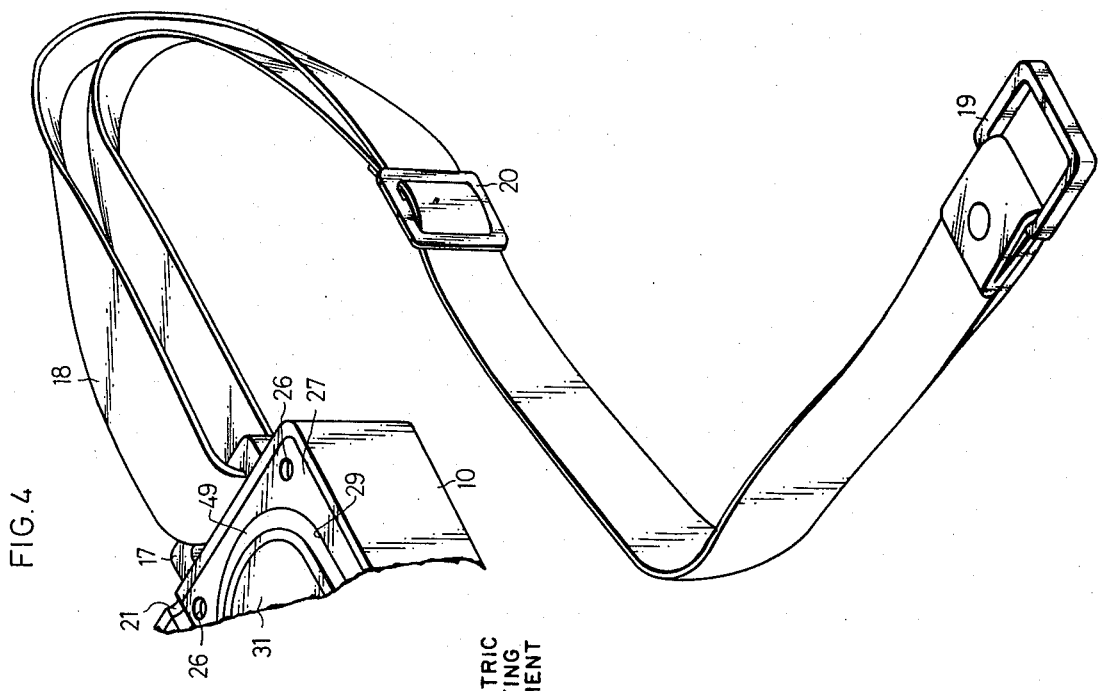
FIG. 4 is a perspective view illustrating the manner in which a hanging band is attached to a case.

A case 10 of the heating device comprises a heater-receiving chamber 11 (see FIGS. 2 and 5) having a front opening and a circuit element-receiving chamber 12 having a rear opening. The case 10 is made of a synthetic material, and a lid 13 thereof is also made of the same material. The case and lid are integrally connected to each other at one side by an integral hinge 70 so that the lid 13 can be opened and closed, and an anchoring projection 14 and a hook 15 are formed on the case 10 and the lid 13 respectively, for keeping the lid 13 closed on the case 10. A display lamp chamber 16 projecting from a front face of the case 10 is formed on the front side of the circuit element-receiving chamber 12 of the case 10. A hanging portion 17 is formed on an upper portion of the case 10, and a band 18 is provided on the hanging portion 17. An annular hanging fixture 19 is attached to a top end of the band 18 as shown in FIG. 4. The length of the band 18 can optionally be adjusted by a length adjusting member 20 so that the case 10 can be hung down at an optional position.

As shown in FIG. 1, an inlet groove 21 having a U-shaped section is formed on an upper edge of the front face of the case 10, and an outlet groove 22 having a U-shaped section is formed on the front side of the circuit element-receiving chamber 12 of the case 10. A temperature control thermistor 23 is attached to the outlet groove 22 to slightly project from the circuit element-receiving chamber 12. In this embodiment, the thermistor 23 is arranged such that standard resistance corresponds to a temperature of 35°±1° C. and a temperature change is detected as a change of quantity of electricity.

Figure 7:
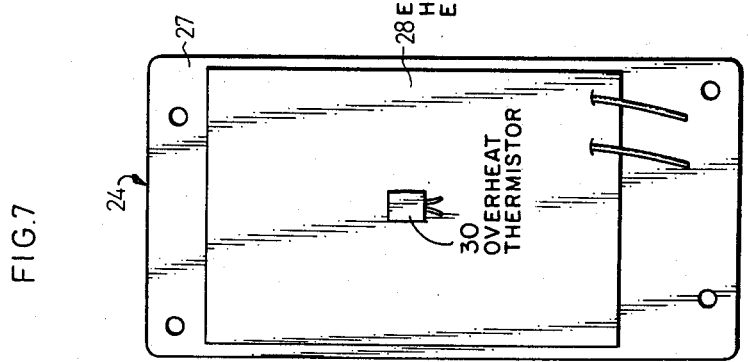
FIG. 7 is a back view of the heater.
Figure 6:
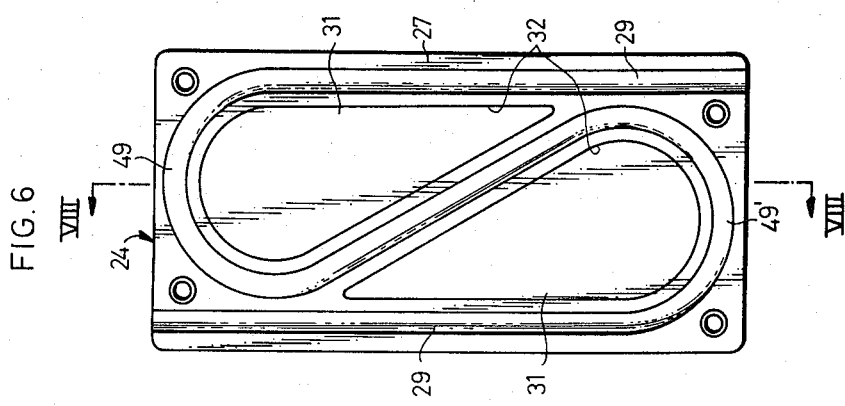
FIG. 6 is a front view of the heater.
Figure 5:
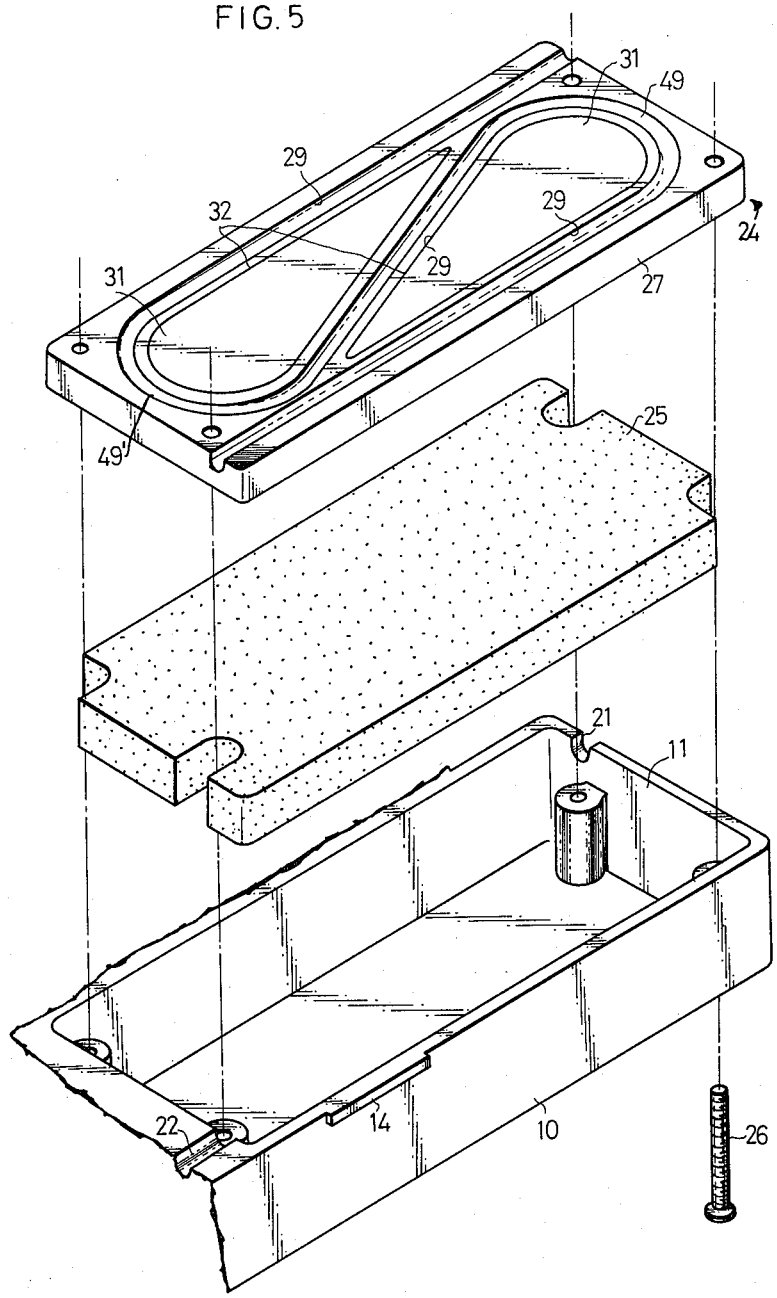
FIG. 5 is a fragmentary perspective view illustrating the manner in which a heater is contained in the heating device.
Figure 8:
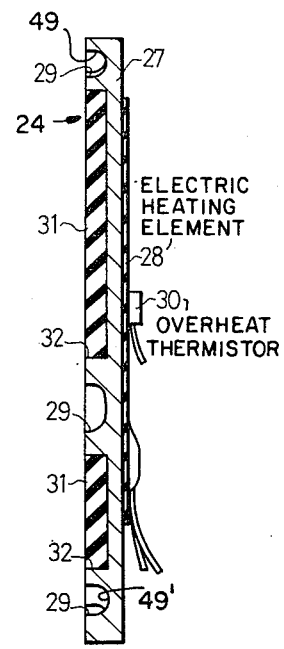
FIG. 8 is a sectional view of the heater taken along line VIII—VIII in FIG. 6.
Figure 9:
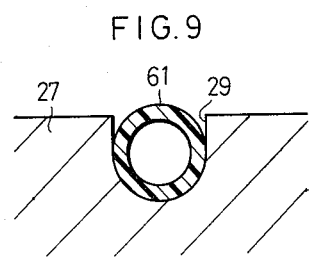
FIGS. 9 and 10 are partial sectional views illustrating the manner in which the liquid feed pipe is situated in a holding groove of the heater.

As shown in FIGS. 1 and 5, a heater 24 is put on a heat insulating material 25, and the heater 24 and the heat insulating material 25 are fixed to the heater-receiving chamber 11 of the case 10 by means of a plurality of screws 26. The heater 24 comprises a heater segment 27 composed of an aluminum plate having an alumite-treated surface and an electric heating element 28 bonded to the back surface of the heater segment 27 by a silicone rubber, as shown in FIGS. 7 and 8, so that discharge of heat is prevented. Preferably, the electric heating element 28 is formed of a heating wire in a layer of rubber. As shown in FIGS. 6 and 9, a holding groove 29 having a U-shaped section is formed on the front surface of the heater segment 27, the groove 29 extending in an S-figured shape to constitute an upper curve 49 and a lower curve 49. The holding groove 29 is slightly smaller than the outer diameter of a liquid feed pipe 61 situated therein. Both ends of the holding groove 29 communicate with the inlet groove 21 and outlet groove 22 of the case 10, respectively. Accordingly, the lower half of the periphery of the liquid feed pipe 61 is intimately contacted with the holding groove 29, and the liquid feed pipe 61 is heated in the meandering S-shape groove 29.

As shown in FIGS. 7 and 8, an overheat sensing thermistor 30 for detecting change of the temperature is fixed to the back surface of the heating element 28 so that the temperature of the heating element 28 is detected and the resistance of the thermistor 30 is drastically reduced when the temperature of the heating element 28 exceeds 63° C. Further, the overheat sensing thermistor 30 has a function of stopping the heating operation of the heating element 28 by this reduction of the resistance. As shown in FIGS. 6 and 8, a silicone rubber 31 is embedded in a recess 32 surrounded by the holding groove 29 of the heater segment 27 to further diminish the thermal capacity of the heater segment 27 composed of aluminum. Since the thermal capacity of the heater segment 27 is thus diminished, when the heater segment 27 is heated at a predetermined temperature by the heating element 28, overshooting owing to excessive heating of the heater proper 27 can be prevented, and it is possible to elevate the temperature of the heater segment 27 to the predetermined level very stably in a short time.

As shown in FIG. 2, control circuit elements 33 are arranged on a printed circuit board (not shown), which is situated in the circuit element-receiving chamber 12 and is supported by a bottom lid 34 disposed on the rear face of the case 10. A pilot lamp 36 is placed in the display lamp chamber 16, and as shown in FIGS. 1 and 3, one end of a cord 37 is connected to the above-mentioned printed circuit through a bush 38 in the lower portion of the case 10 and a plug 39 is connected to the other end of the cord 37.

As particularly shown in FIG. 1, a window 41 is formed on the lid 13 so that when the lid 13 is closed, the display lamp chamber 16 of the case 10 is exposed to the front face and the light of the pilot lamp 36 can be seen from the outside. In the present embodiment, the case 10 and the lid 13 are integrally molded from a soft synthetic resin, so that the lid 13 can be opened and closed by flexibility of the synthetic resin. In a modification of the invention the lid 13 may be connected to the case 10 by means of a hinge or the like so that the lid 13 can be opened and closed.

Figure 10:
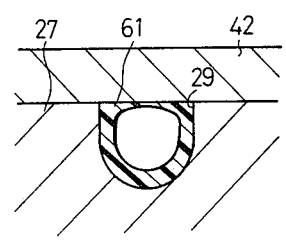
Figure 11:
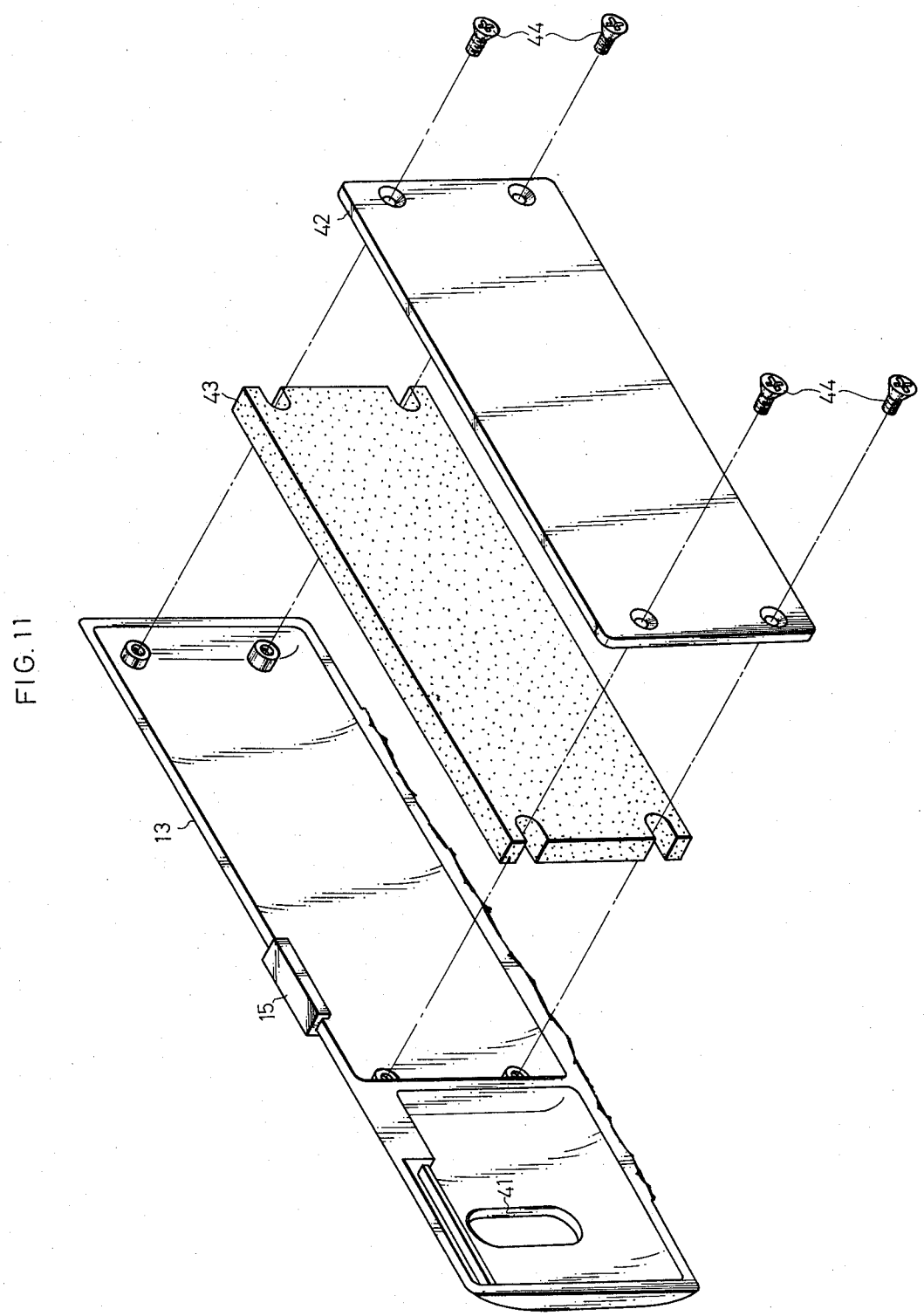
FIG. 11 is a fragmentary perspective view illustrating the manner in which a pressing plate is attached to the lid.

As shown in FIG. 11, a pressing plate 42 made of aluminum is fixed to the inside of the lid 13 by means of screws 44 to prevent the liquid feed pipe 61 situated in the holding groove 29 of the heater segment 27 from falling out from said holding groove 29. A heat insulating material 43 is provided between the pressing plate 42 and the lid 13. Further, this pressing plate 42 presses an upper part of the liquid feed pipe 61 so that the feed pipe 61 is completely contacted with the inner circumferential face of the holding groove 29 as shown in FIG. 10. Accordingly, the periphery of the liquid feed pipe 61 is completely pressed to and contacted with the inner circumferential face of the holding groove 29 and the pressing face of the pressing plate 42, and therefore, wasteful discharge of heat can be prevented at the time of heating and the thermal efficiency can be increased.

Figure 12:
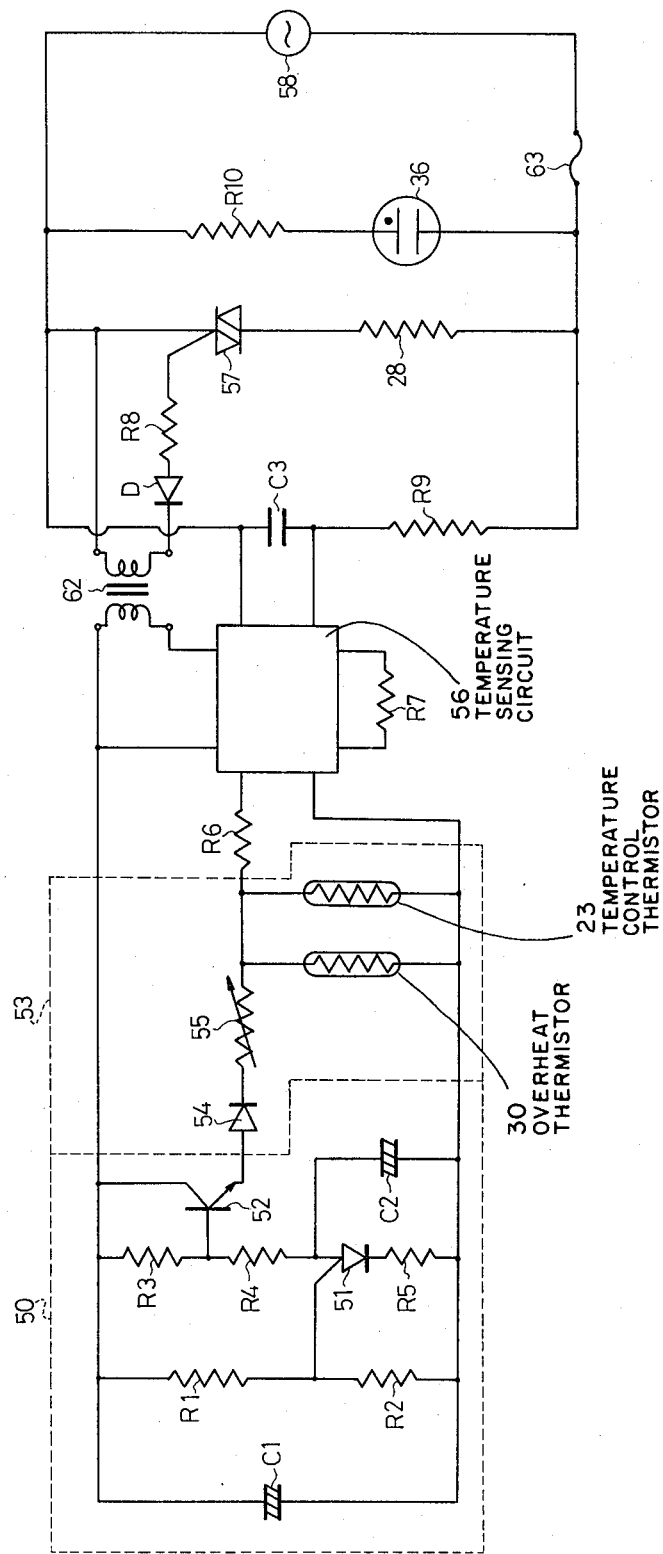
FIG. 12 is an electric circuit diagram of the heating device.

An electric circuit for controlling the heating operation of the heater 24 of the heating device will now be described with reference to FIG. 12.

A clamp wave generating circuit 50 is actuated by a thyristor 51 to generate clamp waves and to transpose impedance of these waves by a transistor 52. The clamp wave generating circuit 50 is connected to a temperature change detecting circuit 53. 15 KΩ, 27 KΩ, 68 KΩ, 390 KΩ and 22Ω are set for bias resistances $R_1$, $R_2$, $R_3$, $R_4$ and $R_5$ of the clamp wave generating circuit 50 of the present embodiment, respectively. 100 μF and 3.3 μF are set for condensers $C_1$ and $C_2$ of the clamp wave generating circuit 50, respectively.

A varistor 54 is connected at one end to the emitter terminal of the transistor 52. The other end of varistor 54 is connected to the aforementioned temperature control thermistor 23 and the overheat sensing thermistor 30 through a variable resistance 55. The overheat thermistor 30 and the temperature control thermistor 23 are connected in parallel to each other and are NTC thermistors. This varistor 54 is disposed to compensate changes of the resistance values of the thermistors 23 and 30 according to temperature changes in the case 10. The variable resistance 55 is designed to make detailed adjustment of changes of the resistance values of the thermistors 23 and 30 according to changes of the temperature.

Changes of the resistance values of the thermistors 23 and 30 are put as output voltages of the temperature change detecting circuit 53 into a temperature sensing circuit 56 which constitutes a zero cross detecting circuit. The sensing circuit 56 compares said output voltages with a certain standard voltage predetermined by the circuit 56, and when the output voltage is higher than the standard voltage, pulse signals generated continuously are applied to a subsequent pulse transformer 62 and when the output voltage is lower than the standard voltage, generation of pulses is stopped. Values of 10 KΩ and 560Ω are set for resistances $R_6$ and $R_7$ for operating the temperature sensing circuit 56, respectively. A triac 57 (bi-directional triode thyristor) has a gate terminal, which is connected to a secondary winding of the pulse transformer 62 through a resistance $R_8$ of 22Ω and a diode D, and the triac 57 is arranged to allow electricity to pass therethrough to the heating element 28 based on the pulse signals from the temperature sensing circuit 56 to generate heat. Accordingly, when no pulse is generated from the temperature sensing circuit 56, the triac 57 is kept in the "off" state, and therefore, heat is not generated by the heating element 28. A condenser $C_3$ is connected between operation power input terminals of the temperature sensing circuit 56 to delay the phase of an input from a power source 58, and in this embodiment, 0.5 μF is set for this condenser $C_3$. $R_9$ is a resistance of 10 KΩ, $R_{10}$ is a resistance of 25 KΩ connected in series to the pilot lamp 36, and reference numeral 63 represents a fuse.

The operation of the electric circuit having the above-mentioned structure will now be described.

The case 10 is hung down by the band 18 for instillation or blood transfusion. As shown in FIG. 3, the liquid feed pipe 61 is situated in the grooves 21, 22 and 29, then the lid 13 is closed and the plug 39 is connected to the power source. At this point, the temperature of the liquid feed pipe 61 is lower than 35°±1° C., so that, the resistance of the temperature control thermistor 23 is maintained at a high level. Accordingly, the voltage fed into the temperature sensing circuit 56 is higher than the standard voltage and pulses are generated to open the triac 57 to thereby cause the heating element 28 to generate heat. Thus, the liquid feed pipe 61 is heated to warm the instillation liquid.

At the time of heating, the liquid feed pipe 61 is intimately contacted with and pressed to the holding groove 29 of the heater segment 27 by the pressing plate 42 disposed on the inside of the lid 13. Therefore, the heat of the heater segment 27 is assuredly conducted to the liquid feed pipe 61 without wasteful radiation of heat from the heater 24. As a result, the thermal efficiency can be improved and uneven heating of the liquid passing through the pipe 61 can be prevented.

Since the liquid feed pipe 61 is bent into S shape in the heater segment 27 and generally the case 10 is situated vertically, the instillation liquid is stored in the lower curved portion 49' of the liquid feed pipe 61 and is heated therein. Also by virtue of this feature, uneven heating of the instillation liquid can be prevented. Further, since the liquid feed pipe 61 is bent into the S shape, the contact area between the liquid feed pipe 61 and the heater segment 27 is increased and the time for passing the liquid through the heater segment 27 is prolonged. Accordingly, uneven heating of the liquid can be prevented completely.

As the instillation liquid is heated, the resistance value of the temperature control thermistor 23 is gradually lowered, and when the temperature of the liquid feed pipe 61 is elevated to 35°±1° C., the voltage fed into the temperature sensing circuit 56 becomes equal to the standard voltage. At this point, generation of pulses is stopped. Accordingly, the triac 57 is then kept in the "off" state to stop generation of heat by the heating element 28, whereby further rise of the temperature of the instillation liquid is prevented. When the temperature is lowered again below 35°±1° C. after a certain time is elapsed the above-mentioned operation is repeated. Therefore, the temperature of the instillation liquid is always maintained at a certain level (35°±1° C.) and at this temperature, instillation is carried out.

When a large quantity of the instillation liquid flows through the liquid feed pipe, heating is carried out in the same manner as described above. However because of a large amount of flow, the thermistor 23 shows a resistance value corresponding to a temperature lower than 35°±1° C. and abnormal heat generation takes place in the heating element 28. This dangerous phenomenon is prevented in the present invention by the following operation.

If the heating element 28 is continuously heated to thereby reach about 63° C., the resistance of the overheat sensing thermistor 30 is abruptly lowered from a high value to a very low value of several Ω. Since this resistance value is much lower than the resistance value of the thermistor 23, an electric current flows through the overheat sensing thermistor 30, whereby the voltage fed into the temperature sensing circuit 56 is lowered below the standard voltage and generation of pulses is stopped. As a result, generation of heat in the heating element 28 is stopped and overheat of the liquid beyond 63° C. can be prevented. Accordingly, even if a large quantity of the instillation liquid flows through the liquid feed pipe 61, instillation can be performed very safely.

As will be apparent from the foregoing illustration, the heating device of the present invention has a very small size not to occupy a large space. Further, the heating device of the present invention can be handled and transferred very easily, and there can be attained an advantage that the operation efficiency of instillation such as dripping or blood transfusion can be remarkably improved.

The present invention has been described in detail with reference to most preferred embodiments. It is apparent that certain changes and modifications may be made without departing from the spirit and scope of the present invention. It is intended that all matter contained in the above description or shown in the accompanying drawing shall be interpreted as illustrative and not in a limiting sense.

What I claim is as my invention:

1. A heating device for instillation comprising a casing having means at one end thereof for vertically supporting the casing during use of the device, said casing including a circuit element receiving chamber and a heater receiving chamber having a front opening, a lid for at least covering said front opening of the heater receiving chamber, a heater situated in said heater receiving chamber, said heater including a heater segment coextensive with, disposed in and filling said front opening and an electric heating element attached to a back side of the heater segment for heating the segment, said heater segment having a tortous groove on a front side thereof for receiving therein a liquid feed pipe through which an instillation liquid to be heated flows, said lid being arranged to cover said groove and feed pipe received therein when in closed position, said groove having upper and lower curves and extending from an upper portion of the heater segment to a lower portion thereof to keep the instillation liquid in the liquid feed pipe between the upper and lower curves for a period sufficient to heat the liquid, and electric circuit means situated in said circuit element receiving chamber, said electric circuit means including first and second temperature control thermistors, the first thermistor sensing temperature of the instillation liquid after passing through the length of the heater segment groove for operating said circuit means to intermittently energize the heating element to heat the instillation liquid flowing through the feed pipe to a predetermined temperature, the second thermistor being provided at the electric heating element for operating said circuit means to turn off the electric circuit means when the electrical heating element is heated beyond a predetermined temperature due to excess flow of the instillation liquid to thereby override the control of the heating element by the first thermistor.

2. A heating device for instillation according to claim 1, in which said lid includes a pressing member to intimately hold a liquid feed pipe in the groove when the lid is closed, insulating materials being provided between the lid and the pressing member and between the casing and the electric heating element.

3. A heating device for instillation according to claim 1, in which the casing and lid are integrally formed of a soft synthetic resin and are joined by an integral hinge portion so that the lid can be freely opened and closed, and an anchoring projection and a hook are provided on the casing and the lid respectively to keep the lid closed.

* * * * *